United States Patent [19]

Mitchell et al.

[11] Patent Number: 5,288,711
[45] Date of Patent: Feb. 22, 1994

[54] METHOD OF TREATING HYPERPROLIFERATIVE VASCULAR DISEASE

[75] Inventors: Robert D. Mitchell, Doylestown, Pa.; Stephen Skwish, Mercer, N.J.

[73] Assignee: American Home Products Corporation, Madison, N.J.

[21] Appl. No.: 874,895

[22] Filed: Apr. 28, 1992

[51] Int. Cl.$^5$ .................... A61K 31/71; A61K 31/725
[52] U.S. Cl. ...................... 514/56; 514/291; 424/122
[58] Field of Search .................. 424/122; 514/291, 56

[56] References Cited

U.S. PATENT DOCUMENTS

| | | | |
|---|---|---|---|
| 3,929,992 | 12/1975 | Sehgal | 424/122 |
| 4,885,171 | 12/1989 | Sehgal | 424/122 |
| 5,078,999 | 1/1992 | Warner | 424/122 |
| 5,080,899 | 1/1992 | Sturm | 424/122 |
| 5,100,899 | 3/1992 | Calne | 514/291 |

OTHER PUBLICATIONS

Drug Res. 39:15 (1989)–Tiozzo.
Circ. Res. 58:839 (1986)–Clowes.
Circ. Res. 56:139 (1985)–Clowes.
Nature 265:625 (1977)–Clowes.
[Proc. Natl. Acad. Sci. U.S.A. 88:8651 (1991)–Bjornsson].
Cell 67:229 (1991)–Klagsbrun.
Arterio 9:147 (1989)–Klein-Soyer.
J. Clin. Invest. 85:2004 (1990)–Lindner.
Molecular and Cellular Biology 12:240 (1992)–Ornitz.
J. Cell Biol. 107:743 (1988)–Saksela.
Science 222:623 (1983)–Thornton.
Eur. Heart J. 12 (Suppl.):386 (1991) de Vries.
JACC 17(2):181A (1991)–Lehmann.
Can. J. Physiol. Pharmacol. 55:48 (1977)–Martel.
FASEB 3, 3411 (1989)–Staruch.
Med. Sci. Res. 17:877 (1989)–Morris.
J. Heart Lung Transplant 11 (pt. 2): 197 (1992)–Gregory.
U.S. Patent Appl. S.N. 07/819,314 filed Jan. 9, 1992--Morris.
J. Heart Lung Transplant 9:55 (1990)–Meiser.
Lancet 388: 1297 (1991)–Meiser.
Am. Heart J. 117:777 (1989)–Ellis.
FASEB 3, 5256 (1989)–Dumont.
Fifth Int. Conf. Inflamm. Res. Assoc. 121 (Abstract) (1990)–Baeder.

*Primary Examiner*—Douglas W. Robinson
*Assistant Examiner*—Jean C. Witz
*Attorney, Agent, or Firm*—Arnold S. Milowsky

[57] ABSTRACT

This invention provides a method of preventing or treating hyperproliferative vascular disease in a mammal by administering an antiproliferative effective amount of a combination of rapamycin and heparin.

13 Claims, No Drawings

METHOD OF TREATING HYPERPROLIFERATIVE VASCULAR DISEASE

BACKGROUND OF THE INVENTION

Many individuals suffer from heart disease caused by a partial blockage of the blood vessels that supply the heart with nutrients. More severe blockage of blood vessels in such individuals often leads to hypertension, ischemic injury, stroke, or myocardial infarction. Typically vascular occlusion is preceded by vascular stenosis resulting from intimal smooth muscle cell hyperplasia. The underlying cause of the intimal smooth muscle cell hyperplasia is vascular smooth muscle injury and disruption of the integrity of the endothelial barrier and the underlying extracellular matrix. The overall disease process can be termed a hyperproliferative vascular disease because of the etiology of the disease process. Under normal circumstances, the cells of the arterial wall can be looked at as being under stringent negative control and in a quiescent non-proliferating state, probably the consequence of contact with their specialized extracellular matrix. Desquamation of the endothelium, resulting in exposure of and possible disruption of the integrity of the extracellular matrix surrounding the cells, leads to 1) a shift in smooth muscle phenotype from a quiescent, contractile state to a migrating, proliferative form [Manderson, J. A., Arterio 9: (3) (1989)], 2) eventual migration of transformed smooth muscle cells from the medial layer to the sub-lesion intimal layer [Clowes, A. W., Circ. Res. 56: 139 (1985)] and 3) subsequent massive proliferation of the intimal smooth muscle layer resulting in arterial luminal blockage [Clowes, A. W., J. Cardiovas. Pharm. 14 (Suppl 6): S12 (1989)]. Investigations of the pathogenesis of intimal thickening have shown that, following arterial injury, platelets, endothelial cells, macrophages and smooth muscle cells release paracrine and autocrine growth factors (such as platelet derived growth factor, epidermal growth factor, insulin-like growth factor, and transforming growth factor) and other cytokines that result in the smooth muscle cell proliferation and migration. T-cells and macrophages also migrate into the neointima. [Haudenschild, C., Lab. Invest. 41: 407 (1979); Clowes, A., Circ. Res. 56: 139 (1985); Clowes, A., J, Cardiovas. Pharm. 14 (Suppl. 6): S12 (1989); Manderson, J., Arterio. 9: 289 (1989); Forrester, J., J. Am. Coll. Cardiol. 17: 758 (1991)]. This cascade of events is not limited to arterial injury, but also occurs following injury to veins and arterioles.

Vascular injury causing intimal thickening can be broadly categorized as being either biologically or mechanically induced. Atherosclerosis is one of the most commonly occurring forms of biologically mediated vascular injury leading to stenosis. The migration and proliferation of vascular smooth muscle plays a crucial role in the pathogenesis of atherosclerosis. Atherosclerotic lesions include massive accumulation of lipid laden "foam cells" derived from monocyte/macrophage and smooth muscle cells. Formation of "foam cell" regions is associated with a breech of endothelial integrity and basal lamina destruction. Triggered by these events, restenosis is produced by a rapid and selective proliferation of vascular smooth muscle cells with increased new basal lamina (extracellular matrix) formation and results in eventual blocking of arterial pathways. [Davies, P. F., Artherosclerosis Lab. Invest. 55: 5 (1986)].

Until recently, it was generally believed that this proliferation resulted from growth factors released from platelets deposited on the newly exposed matrix surface. However, recent data suggests that this phenomena occurs as a consequence of an intimate interplay between at least three components of the extracellular matrix which act strongly to influence smooth muscle cell phenotype and/or response. These components include: 1) matrix collagen and its subtypes, 2) matrix bound growth factors such as fibroblast growth factor (FGF) and transforming growth factor-$\beta$ (TGF-$\beta$), and 3) the matrix bound proteoglycans, predominantly those containing heparan sulfate glycosaminoglycan chains.

Mechanical injuries leading to intimal thickening result following balloon angioplasty, vascular surgery, transplantation surgery, and other similar invasive processes that disrupt vascular integrity. Intimal thickening following balloon catheter injury has been studied in animals as a model for arterial restenosis that occurs in human patients following balloon angioplasty. Clowes, Ferns, Reidy and others have shown that deendothelialization with an intraarterial catheter that dilates an artery injures the innermost layers of medial smooth muscle and may even kill some of the innermost cells. [Schwartz, S. M., Human Pathology 18: 240 (1987); Fingerle, J., Arteriosclerosis 10: 1082 (1990)] Injury is followed by a proliferation of the medial smooth muscle cells, after which many of them migrate into the intima through fenestrae in the internal elastic lamina and proliferate to form a neointimal lesion.

Vascular stenosis can be detected and evaluated using angiographic or sonographic imaging techniques [Evans, R. G., JAMA 265: 2382 (1991)] and is often treated by percutaneous transluminal coronary angioplasty (balloon catheterization). Within a few months following angioplasty, however, the blood flow is reduced in approximately 30–40 percent of these patients as a result of restenosis caused by a response to mechanical vascular injury suffered during the angioplasty procedure, as described above. [Pepine, C., Circulation 81: 1753 (1990); Hardoff, R., J. Am. Coll. Cardiol. 15 1486 (1990)].

It has been shown that heparin inhibits smooth muscle cell growth both in culture and in vivo. [Tiozzo, R., Arzneim. Forsch./Drug. Res. 39: 15 (1989)]; [Clowes, A. W., Circ. Res. 58 (6): 839 (1986); Clowes, A. W., Circ. Res. 56: 139 (1985)]. As early as 1977, Clowes and Karnovsky [Clowes, A. W., Nature 265: 625 (1977)] showed that administration of commercial heparin to animals whose carotid arteries have been injured in order to produce a myointimal plaque dramatically reduced the size of the myointimal thickening. The authors, showed that the effect of heparin on the injured arterial wall was to inhibit the growth of smooth muscle cells and that this effect was, in no way, related to the anti-coagulant activity of the heparin. Heparin, through its obligatory role in promoting growth factor binding, also has been shown to promote endothelial growth, a necessary element of vascular healing following vascular injury. [Bjornsson, M., Proc. Natl. Acad. Sci. USA 88: 8651 (1991); Klagsburn, M., Cell 67: 229 (1991); Klein-Soyer, C., Arterio. 9: 147 (1989); Lindner, V. J. Clin. Invest. 85: 2004 (1990); Ornitz, D. M., Molecular and Cellular Biology 12: 240 (1992); Saksela, O., J. Cell Biol. 107: 743 (1988); Thornton, S. C., Science 222: 623 (1983)]. De Vries has also reported efficacious results in preventing restenosis in clinical studies with heparin

[Eur. Heart J. 12 (Suppl.): 386 (1991)], however, Lehmann reported that chronic use of heparin (1000 units/day, s.c.) after successful coronary angioplasty paradoxically appears to increase the likelihood of restenosis, and caused abnormal bleeding in 41% of patients in the study. [JACC 17(2): 181A (1991)].

Rapamycin, a macrocyclic triene antibiotic produced by *Streptomyces hygroscopicus* [U.S. Pat. No. 3,929,992] has been shown to prevent the formation of humoral (IgE-like) antibodies in response to an albumin allergic challenge [Martel, R., Can. J. Physiol. Pharm. 55: 48 (1977)], inhibit murine T-cell activation [Staruch, M., FASEB 3: 3411 (1989)], prolong survival time of organ grafts in histoincompatible rodents [Morris, R., Med. Sci. Res. 17: 877 (1989)], and inhibit transplantation rejection in mammals [U.S. Pat. No. 5,100,899]. Rapamycin has also has been shown to inhibit proliferation of vascular smooth muscle cells in vitro in response to mitogenic and heterotrophic factors, and in vivo following balloon catheterization of the carotid artery. [Morris, R., J. Heart Lung Transplant. 11 (pt. 2): 1992)].

DESCRIPTION OF THE INVENTION

This invention provides a method of preventing or treating hyperproliferative vascular disease in a mammal in need thereof by administering an antiproliferative effective amount of a combination of rapamycin and heparin to said mammal orally, parenterally, intravascularly, intranasally, intrabronchially, transdermally, rectally, or via a vascular stent impregnated with a combination of rapamycin and heparin.

As such, the combination of rapamycin and heparin is useful in preventing or treating intimal smooth muscle cell hyperplasia, restenosis, and vascular occlusion in a mammal, particularly following either biologically or mechanically mediated vascular injury, or under conditions that would predispose a mammal to suffering such a vascular injury. Biologically mediated vascular injury includes, but is not limited to injury attributed to autoimmune disorders; alloimmune related disorders; infectious disorders including endotoxins and herpes viruses such as cytomegalovirus; metabolic disorders such as atherosclerosis; and vascular injury resulting from hypothermia, hypothermia, and irradiation. Mechanically mediated vascular injury includes, but is not limited to vascular injury caused by catheterization procedures or vascular scraping procedures such as percutaneous transluminal coronary angioplasty; vascular surgery; transplantation surgery; laser treatment; and other invasive procedures which disrupt the integrity of the vascular intima or endothelium.

Preventing includes the prophylactic prevention of hyperproliferative vascular disease in a susceptible mammal and treating includes arresting the development, and retarding the progression of hyperproliferative vascular disease in a susceptible mammal.

Administration can also be accomplished via mixed routes of administration. For example, rapamycin may be given orally and heparin given parenterally. A vascular stent can be impregnated with either rapamycin or heparin, and the other component of the combination can be administered orally or parenterally. Other permutations of mixed modes of administration will be appreciated by one skilled in the art.

The effect of the combination of rapamycin and heparin on hyperproliferative vascular disease was established in a standard pharmacological test procedure that emulates the hyperproliferative effects observed in mammals that are undergoing intimal smooth muscle proliferation and are therefore developing restenosis. The procedure used and the results obtained are described below.

Primary rat aorta smooth muscle cell cultures from passage 2–10 were grown to confluence in 100 mm culture dishes (Falcon, 1029) in media 199 (M199; Gibco 320 1150AJ) plus 10% fetal bovine serum (FBS, Gibco 240 6000AG). Cells were washed with calcium, magnesium free Delbecco's phosphate buffered saline (-D-PBS; Gibco, 310-4190AJ) and trypsinized (Gibco, 610-5050AG) for five minutes. Cells were scraped from culture dishes with a rubber policeman and centrifuged out of enzyme (10 minutes × 1000 g). Cells were resuspended in M199 plus 10% FBS containing ($^3$H)-thymidine (0.5 $\mu$Ci/mL) at 8–15,000 cells/mL, and were plated into either 24 (Falcon, 3047) or 96 (Costar 9102) well plates (1 mL in 24 well plate and 200 $\mu$L in 96 well plates.) Drugs were added to each well (20 $\mu$L in 24 well plates and 4 $\mu$L in 96 well plate; 50 fold dilution) and plates were incubated for 24 hours at 37°; 5% $CO_2$. Plates were placed on ice and washed three times with ice cold DeBelco's phosphate buffered saline (D-PBS; Gibco 310-4040AJ) and were incubated in ice cold 10% trichloroacetic acid (TCA) for 30 minutes to remove acid soluble proteins (leaving only cell superstructure and DNA). Plates were washed three times with TCA and aspired dry. 96-well plates were snapped apart and placed in scintillation vials, scintillated (10 mL/vial) and counted. 24-well plates were treated with 0.4N NaOH (250 $\mu$L/well) for 3–4 hours to solubilize cells. Solution was transferred to scintillation vials containing 0.4N HCl (250 $\mu$L/vial; to neutralize NaOH) and each well was rinsed two times with water (250 $\mu$L) for a total volume of 1 mL/vial. Vials were scintillated (10 mL/vial) and counted.

The following table shows the results obtained for the combination of rapamycin and heparin on rat aortic smooth muscle cell proliferation.

| EFFECT OF HEPARIN AND RAPAMYCIN ON CULTURED RAT AORTIC SMOOTH MUSCLE CELL PROLIFERATION (VALUES EXPRESSED AS % OF CONTROL ± STANDARD DEVIATION) | | | | | | | |
|---|---|---|---|---|---|---|---|
| RAP (nM) | HEPARIN ($\mu$g/ml) | | | | | | |
| | 0 | 0.1 | 1.0 | 10 | 25 | 50 | 200 |
| 0 | 100 ± 1.3 | 101.7 ± 5.1 | 67.2 ± 6.5 | 53.2 ± 2.2 | 38.1 ± 1.9 | 31.5 ± 0.5 | 25.1 ± 1.9 |
| 0.01 | 100.6 ± 3.1 | 102.4 ± 4.4 | 65.1 ± 2.8 | 47.5 ± 2.0 | 36.5 ± 0.8 | 29.1 ± 1.4 | 26.0 ± 1.7 |
| 0.1 | 97.8 ± 2.7 | 104.6 ± 7.0 | 61.0 ± 5.2 | 43.9 ± 3.3 | 29.7 ± 2.5 | 23.8 ± 0.7 | 20.1 ± 1.0 |
| 1.0 | 70.1 ± 1.7 | 75.7 ± 4.3 | 45.6 ± 5.9 | 24.4 ± 0.4 | 13.7 ± 0.3 | 12.0 ± 0.3 | 9.7 ± 0.6 |
| 10.0 | 56.0 ± 2.9 | 53.7 ± 2.3 | 28.7 ± 2.4 | 17.9 ± 0.7 | 11.1 ± 0.5 | 4.4 ± 1.4 | 3.8 ± 1.1 |
| 100.0 | 50.5 ± 3.0 | 50.0 ± 2.3 | 29.0 ± 2.2 | 17.2 ± 1.1 | 10.1 ± 0.2 | 4.4 ± 1.2 | 3.8 ± 0.8 |

The results of this standard test procedure demonstrates that the combination of rapamycin and heparin prevented vascular smooth muscle cell proliferation, and is therefore useful in preventing or treating hyperproliferative vascular disease. Specifically, the combination of rapamycin and heparin is useful in preventing or treating intimal smooth muscle cell hyperplasia, restenosis, and vascular occlusion in a mammal, particularly following either biologically or mechanically mediated vascular injury, or under conditions that would predispose a mammal to suffering such a vascular injury.

While the results also show that rapamycin and heparin each are separately effective in preventing vascular smooth muscle cell proliferation, the combination of rapamycin with heparin is distinctly advantageous over either monotherapy as the combination takes advantage of the beneficial aspects of each agent, while minimizing the negative aspects of each agent. Rapamycin is a relatively nonselective, potent antiproliferative agent which inhibits both intimal smooth muscle cell proliferation as well as endothelial cell growth. As endothelial regrowth is necessary to prevent the occurrence of restenosis following the cessation of treatment, it can be expected the nonselective antiproliferative properties of rapamycin would require lengthy treatment periods to provide for endothelial healing. In contrast, heparin has relatively selective antiproliferative properties. Heparin has been shown to prevent smooth muscle cell growth, while promoting endothelial cell growth, thereby inhibiting intimal narrowing, and promoting vascular endothelial healing. [Bjornsson, M., Proc. Natl. Acad. Sci. USA 88: 8651 (1991); Klagsburn, M., Cell 67: 229 (1991); Klein-Soyer, C., Arterio. 9: 147 (1989); Lindner, V. J. Clin. Invest. 85: 2004 (1990); Ornitz, D. M., Molecular and Cellular Biology 12: 240 (1992); Saksela, O., J. Cell Biol. 107: 743 (1988); Thornton, S. C., Science 222: 623 (1983)]. It has been shown that upon reestablishment of the endothelial layer following vascular injury, intimal smooth muscle cell proliferation ceases and restenosis is therefore arrested. [Reidy, M., Lab. invest. 59: 36 (1988); Chevru, A., Surg. Gynecol. Obstet. 171: 443 (1990); Fishman, J., Lab. Invest. 32: 339 (1975); Haudenschild, C., Lab. Invest 41: 407 (1979)]. Heparin therapy therefore provides the beneficial therapeutic profile of promoting endothelial healing while suppressing intimal smooth muscle cell proliferation. Treatment with heparin, however, is not without side effects. In addition to acting as an antiproliferative agent, heparin is also a powerful anticoagulant, and can cause hemorrhage. [Ellis, S., Am. Heart J. 117: 777 (1989)]. Antibodies to heparin also develop during chronic heparin administration which bind to platelets leading to thrombocytopenia.

As shown in Table 1, the use of rapamycin in combination with heparin provides for dramatically reduced dosages of each agent to produce the same effect. For example, at a combination dose of 1.0 nM rapamycin and 10 μg/mL heparin, smooth muscle cell proliferation occurs is inhibited by 76% (24% of control level), whereas a dose of 200 μg/mL of heparin alone is needed to achieve this degree of inhibition. A dose of 100 nM rapamycin was not able to prevent smooth muscle cell proliferation to this extent. By achieving efficacious results at lower doses of each agent, the negative aspects of each agent can be alleviated. The combined use of rapamycin and heparin allows a minimization of the dose of rapamycin used, as such, the antiproliferative effect on endothelial cell growth is expected to be negated by the proliferative effect of heparin on the endothelium. Additionally, by using lower doses of heparin, the dose dependent side effects associated with heparin can be avoided.

Based on this disclosure, other advantages of using rapamycin in combination with heparin for preventing or treating hyperproliferative vascular disorders will be apparent to one skilled in the art.

When rapamycin is employed in combination with heparin in the prevention or treatment of hyperproliferative vascular disease, it can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Rapamycin in combination with heparin may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. Rapamycin in combination with heparin may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

Rapamycin in combination with heparin can be administered intravascularly or via a vascular stent impregnated with rapamycin in combination with heparin, during balloon catheterization to provide localized effects immediately following injury.

Rapamycin in combination with heparin may be administered topically as a solution, cream, or lotion by formulation with pharmaceutically acceptable vehicles containing 0.1–5 percent, preferably 2%, of active compound.

The dosage requirements vary with the particular compositions employed, the route of administration, the severity of the symptoms presented and the particular subject being treated. Based on the results obtained in the standard pharmacological test procedures, projected daily dosages of rapamycin, when administered in combination with heparin, would be 0.005–50 mg/kg and preferably between 0.05–10 mg/kg. Since non-anticoagulant heparin and anticoagulant heparins are equally effective, dosage for heparin should be established on a mg/kg basis preferably between 1–100 mg/kg, noting that at higher combinations of heparin, a non-anticoagulant form is preferred to avoid hemorrhagic side effects.

Treatment will generally be initiated with small dosages less than the optimum dose of the compound. Thereafter the dosage is increased until the optimum effect under the circumstances is reached; precise dosages for oral, parenteral, intravascular, intranasal, intrabronchial, transdermal, or rectal administration will be determined by the administering physician based on experience with the individual subject treated. In general, the combination of rapamycin and heparin is most desirably administered at a concentration that will generally afford effective results without causing any harmful or deleterious side effects, and can be administered either as a single unit dose, or if desired, the dosage may be divided into convenient subunits administered at suitable times throughout the day.

What is claimed is:

1. A method of treating vascular disease resulting from smooth muscle cell proliferation in a mammal in need thereof which comprises, administering an antiproliferative effective amount of the combination of rapamycin in a concentration of at least 1 nM and heparin in a concentration of at least 1 μg/ml to said mammal orally, parenterally, intravascularly, intranasally, intrabronchially, transdermally, rectally, or via an impregnated vascular stent.

2. The method according to claim 1 wherein the vascular disease resulting from smooth muscle cell proliferation is intimal smooth muscle cell hyperlasia or restenosis.

3. The method according to claim 2 wherein the combination of rapamycin and heparin is administered concurrent with said mammal undergoing a percutaneous transluminal coronary angioplasty procedure.

4. The method according to claim 3 wherein the hyperproliferative vascular disease is restenosis.

5. The method according to claim 2 wherein the combination of rapamycin and heparin is administered subsequent to said mammal undergoing a percutaneous transluminal coronary angioplasty procedure.

6. The method according to claim 5 wherein the hyperproliferative vascular disease is restenosis.

7. The method according to claim 2 wherein the combination of rapamycin and heparin is administered concurrent with said mammal sustaining a biologically or mechanically mediated vascular injury.

8. The method according to claim 2 wherein the combination of rapamycin and heparin is administered subsequent to said mammal sustaining a biologically or mechanically mediated vascular injury.

9. A composition for the use in preventing or treating hyperproliferative vascular disease in a mammal which comprises an antiproliferative effective amount of a combination of rapamycin in a concentration of at least 1 nM and heparin in a concentration of at least 1 μg/ml and a pharmaceutically acceptable carrier.

10. The composition according to claim 9 wherein the vascular disease resulting from smooth muscle cell proliferation is intimal smooth muscle cell hyperplasia or restenosis.

11. The method according to claim 1 wherein the vascular disease resulting from smooth muscle cell proliferation is vascular occlusion.

12. The composition according to claim 9 wherein the vascular disease resulting from smooth muscle cell proliferation is vascular occlusion.

13. A method of treating restenosis in a mammal resulting from said mammal undergoing a percutaneous transluminal coronary angioplasty procedure which comprises administering an antirestenosis effective amount of a combination of rapamycin and heparin to said mammal orally, parenterally, intravascularly, intranasally, intrabronchially, transdermally, rectally, or via an impregnated vascular stent.

* * * * *